United States Patent [19]

Martino et al.

[11] Patent Number: 5,256,404
[45] Date of Patent: Oct. 26, 1993

[54] GRANULAR STARCH AS SUNSCREEN AGENT IN AQUEOUS COMPOSITIONS

[75] Inventors: Gary T. Martino, Plainsboro; Joseph Pasapane, Morristown; Frank A. Nowak, Somerville, all of N.J.

[73] Assignee: National Starch and Chemical Investment Holding Corporation, Wilmington, Del.

[21] Appl. No.: 930,865

[22] Filed: Aug. 14, 1992

[51] Int. Cl.$^5$ .................. A61K 7/42; A61K 7/44; A61K 7/48
[52] U.S. Cl. ........................ 424/59; 424/60; 514/844; 514/847; 514/937; 514/938
[58] Field of Search ................... 424/59, 60

[56] References Cited

U.S. PATENT DOCUMENTS

| | | | |
|---|---|---|---|
| 3,485,915 | 12/1969 | Gerstein et al. | 424/60 |
| 3,852,475 | 12/1974 | Tarangul | 424/361 |
| 4,401,649 | 8/1983 | Green | 424/60 |
| 4,857,307 | 8/1989 | Suss et al. | 424/63 |
| 4,894,222 | 1/1990 | Matravers | 424/59 |
| 4,917,883 | 4/1990 | Strobridge | 424/59 |
| 4,935,533 | 6/1990 | Gosciniak | 558/388 |
| 5,026,540 | 6/1991 | Dixos et al. | 424/60 |

*Primary Examiner*—Dale R. Ore
*Attorney, Agent, or Firm*—Eugene Zagarella, Jr.

[57] ABSTRACT

A sunscreen composition comprising a natural based uncooked, granular starch material as the sunscreen agent incorporated in a pharmaceutically acceptable aqueous based starch carrier.

18 Claims, No Drawings

GRANULAR STARCH AS SUNSCREEN AGENT IN AQUEOUS COMPOSITIONS

BACKGROUND OF THE INVENTION

This invention relates to the use of a natural-based starch material as a sunscreen agent in aqueous sunscreen compositions.

The harmful effects from excessive exposure of human skin to ultraviolet radiation from the sun and other sources is well known. The need to protect human skin from ultraviolet radiation, particularly solar radiation, has been well documented in recent years and a variety of sunscreen preparations have been developed to provide varying degrees of screening or blocking protection.

Sunscreens are of two types, physical and chemical. Physical screening agents, such as titanium dioxide and zinc oxide, are opaque materials that block and scatter light and therefore act as mechanical barriers. Chemical screening agents act by absorbing ultraviolet light and offer selective protection against certain ultraviolet wave bands depending on their absorption spectrum. Anthranilates, cinnamates, benzyl and homomenthyl salicylate and aminobenzoic acid and its ester derivatives are absorbing sunscreen agents of this type.

Sunscreen compositions are generally available in various forms such as creams, lotions and oils containing the active sunscreen agent disposed in a pharmaceutically acceptable carrier. Illustrative compositions are shown in U.S. Pat. No. 4,917,883 which discloses an oil-in-water emulsion sunscreen composition containing selected film formers and sunscreen agents such as aminobenzoate esters; U.S. Pat. No. 5,026,540 which discloses a clear, waterproof sunscreen composition comprising a film forming vinylpyrrolidone copolymer, a sunscreening agent and an emollient; and U.S. Pat. Nos. 4,401,649 and 4,935,533 which disclose sunscreen compositions containing respectively selected aminobenzoate esters of alkylene diols or polyols and 1-cyclohexenylacetonitrile derivatives as sunscreen agents. U.S. Pat. No. 4,894,222 discloses a waterproof sunscreen formulation comprising a mixture of an aliphatic wax and anhydrous hydrophobic starch as its waterproofing agents in a water-free carrier containing one or more conventional Uv absorbers as the sunscreen agent.

For topical applications to the skin, sunscreen compositions must be nontoxic and non-irritating to the skin tissue and capable of application as a continuous film. In addition, the active sunscreening agent must be chemically stable and in particular must be resistant to chemical and photodegradation when on the skin as well as resistant to absorption through the skin.

SUMMARY OF THE INVENTION

Now, in accordance with this invention, it has been found that natural based starch materials are useful as sunscreen agents, are not irritating to the skin nor absorbed through the skin, and are particularly effective in aqueous sunscreen compositions provided in the form of water containing emulsions.

More particularly, this invention is directed to a sunscreen composition comprising a pharmaceutically acceptable aqueous based carrier having incorporated therein an effective amount of uncooked, granular starch as the sunscreen agent.

DETAILED DESCRIPTION OF THE INVENTION

This invention relates to the use of natural-based starch materials as the sunscreen agent or ultraviolet (UV) block in aqueous sunscreen compositions.

The starch sunscreen agents used in this invention may be any uncooked, granular starch. It is well known that starch in its natural state exists in the form of discrete granules, which in the presence of water and heat or certain chemicals (such as strong alkalis) undergo gelatinization. The phenomenon of gelatinization involves the swelling, rupture and disintegration of the starch granules, so that they disperse in water to form a homogeneous hydrated colloidal dispersion. This gelatinization and dispersion of the granules is also referred to as cooking. It is important that the starch material used in this invention be in its naturally occurring granular form and is predominantly or essentially uncooked or ungelatinized.

The starch sunscreen agents of this invention may be any uncooked, granular starch either native or modified. Such starches include those derived from any plant source including corn, potato, rice, wheat, tapioca, waxy maize and high amylose corn. The starch may bemodified or unmodified. By modified it is meant that the starch can be derivatized or altered by typical processes known in the art, e.g., esterification, etherification, oxidation, acid hydrolysis, crosslinking and enzyme conversion. Particularly useful modified starches are the hydrophobic starch derivatives containing an ether, simple ester, or half-acid ester substituent with a saturated or unsaturated hydrocarbon chain of at least 5, preferably 5 to 22, carbon atoms. Alkenyl succinate starches are a common and preferred hydrophobically modified starch and are prepared by the reaction of alkenyl-succinic anhydrides with starch.

The use of starch as a sunscreen agent provides the sunscreen composition of this invention with protection against Uv radiation in both the UVA and UVB wavelength range. The starch material may be used alone, in mixtures thereof or in combination with other known UVA or UVB absorbers to provide varying sun protection factors (SPF) in human subjects under different conditions.

The amount of starch used will be an effective Uv absorbing amount, more particularly the sunscreen compositions contain from about 0.5 to 30%, preferably from about 2 to 15% by weight of starch, based on the weight of the composition.

The sunscreen compositions of this invention contains a pharmaceutically acceptable starch sunscreen carrier. The term "pharmaceutically acceptable starch sunscreen carrier" is intended to include any vehicle or medium capable of incorporating the starch sunscreen agent in a manner permitting uniform topical application and also is dermatologically innocuous and cosmetically acceptable. The carrier used in this invention will be water-based and may include oils, fats, waxes, synthetic polymers, and emulsifiers. Preferably the carrier will be an aqueous emulsion, i.e., either water-in-oil or oil-in-water.

As noted, the sunscreen compositions of this invention will be aqueous or water-based. Generally, water is present in an amount of from about 20 to 99.5% by weight, based on the weight of the composition and preferably from about 30 to 90%.

Aqueous emulsions are the preferred carrier for the sunscreen compositions of this invention and include creams and lotions. These emulsions which comprise water-based and oil-based phases, may be oil-in-water emulsions having oil as the dispersed phase and water as the continuous phase or they may be water-in-oil emulsions with water dispersed in oil, which is the continuous phase. The oil phase is typically made up of cosmetically acceptable or conventional oily substances that are soluble in this phase, such as oils, waxes and emulsifiers. Compounds which can be included in the oil phase are typically mineral, animal and vegetable oils and fats, synthetic esters or fatty acids with aliphatic alcohols, higher fatty alcohols, waxes, so called mineral fats and oils such as paraffin oil, petrolatum, ceresin, silicone oils and silicone fats. The water phase will include water and water soluble components such as alkalis, alkanolamines, polyhydric alcohols and preservatives.

The emulsions, as described above, include one or more emulsifiers which usually are contained in the oil phase but in some instances, depending on the type, may be in the water phase. Emulsifiers, which may be ionic or nonionic are well known and constitute a large group of conventional and commercially available products. They are often characterized by their hydrophilic-lipophilic balance (HLB). Oil-in-water (O/w) emulsifying agents typically have an HLB of more than 6.0 and produce emulsions in which the continuous phase is hydrophilic and such emulsions are generally dispersible in water. Emulsifiers of this type include PEG 300 distearate, sorbitan monolaurate and triethanolamine stearate. Water-in-oil (W/o) emulsifiers usually have an HLB of less than 6.0, preferably below 5, and produce emulsions in which the continuous phase is lipophilic. Such emulsifiers include lanolin alcohols, ethylene glycol monostearate, sorbitan monooleate and PEG 200 dilaurate. Emulsifiers with HLB's of between 5 and 7 may function as either W/0 or 0/w emulsifiers depending on how they are used.

The amount of emulsifiers used in the emulsions of this invention can vary depending on the system and typically will be an effective emulsifying amount. More particularly, the amount of emulsifier can vary from about 0.1 to 2s% by weight, based on the weight of the oil phase and preferably from about 1 to 10%.

The pharmaceutically-acceptable starch sunscreen carriers typically comprise from about 70 to 99.5% by weight, based on the weight of the sunscreen composition and preferably from about 85 to 98%.

The pharmaceutically-acceptable starch sunscreen carrier used in the composition of the present invention may also contain in addition to the aforementioned components, a wide variety of other oil soluble materials and/or water soluble materials. Additionally, the carrier may contain additives other than those specifically mentioned herein, for example, agents suitable for aesthetic purposes such as perfumes and/or dyes.

Among the oil soluble materials are non-volatile silicone fluids such as dimethicones, cyclomethicones and polydimethyl siloxanes with viscosities ranging from about 10 to 100,000 centistokes at 25° C. These siloxanes are available from Dow Corning Corporation as the Dow Corning 200 series. Cyclomethicones are available in the 300 series.

Other oil soluble materials include fatty acid alcohols such as cetyl alcohol and stearyl alcohol; esters such as cetearyl palmitate, lauryl myristate and isopropyl palmitate; oils such as castor oil, jojoba oil, cottonseed oil, peanut oil and sesame oil; waxes such as petrolatum, ceresin wax, carnauba wax, beeswax, and castor wax; cetyl palmitate and glyceryl tribehenate; and lanolin, its derivatives and components such as acetylated lanolin, lanolin alcohols and lanolin fatty acids. Sterols such as soyasterol, cholesterol and phytosterol are also useful herein. Highly preferred for use herein are isodecyl neopentanoate, isohexadecane and $C_{12}$–$C_{15}$ alcohols benzoate (available as Finsolv TN from Finetex).

These optional oil phase materials may individually comprise up to about 20% by weight of the total sunscreen composition, preferably from about 5 to 15%.

Additional water soluble materials may also be present in the compositions of this invention. Included are humectants such as glycerine, hexylene glycol, sorbitol, propylene glycol, alkoxylated glucose and hexanetriol; tyrosine; thickening agents such as carboxyvinyl polymers (offered by B. F. Goodrich Company under the trademark Carbol®, such polymers are described in detail in U.S. Pat. No. 2,798,053, issued July 2, 1957 to Brown, incorporated herein by reference); ethyl cellulose, polyvinyl alcohol, carboxymethyl cellulose, vegetable gums and clays such as Veegum ® (magnesium aluminum silicate, R. T. Vanderbilt, Inc.); proteins and polypeptides; preservatives such as the methyl, ethyl, propyl and butyl esters of hydroxybenzoic acid (Parabens-Mallinckrodt Chemical Corp.), EDTA, methylisothiazolinone and imidazolidinyl ureas (Germall 115 - Sutton Laboratories); and pH controlling agents such as sodium hydroxide, potassium hydroxide or citric acid, if desired.

Additional materials which may be used in this composition include UV scattering powders or absorbing materials, e.g., titanium dioxide, oxybenzone, sulisobenzone, menthyl anthranilate, aminobenzoic acid, 2-ethoxy p-methoxy cinnamate, digalloyl trioleate, 2-ethylhexyl salicylate, glyceryl aninobenzoate and antioxidants such as BHT, BHA, propyl gallate, ascorbic and citric acid, as well as chelators such as disodium EDTA.

The water phase materials may individually comprise up to about 25% by weight of the total sunscreen composition, preferably up to about 15%.

The following examples further illustrate the embodiments of this invention. In the example all parts and percentages are given by weight and all temperatures in degrees Celsius unless otherwise noted.

EXAMPLE 1

A hydrophobic starch, aluminum starch octenylsuccinate was formulated into a sunscreen lotion in the following manner:

|  | Parts by Weight |
|---|---|
| Phase A | |
| Isocetyl alcohol | 7.00 |
| Finsolv TN - $C_{12}$–$C_{15}$ alcohols benzoate | 8.00 |
| Stearic acid T.P. | 2.00 |
| PEG-40 stearate | 2.00 |
| Dimethicone copolyol | 1.00 |
| Cetyl alcohol | 1.00 |
| Glyceryl stearate | 0.50 |
| Dimethyl stearamine | 1.00 |
| Acrylates/t-octylpropenamide copolymer | 2.00 |
| Phase B | |
| Deionized water | 54.25 |
| Carbomer 941 (2% solution) | 10.00 |
| Methylparaben | 0.15 |
| Propylparaben | 0.10 |

|  | Parts by Weight |
|---|---|
| Triethanolamine (99%) | 0.80 |
| Phase C | |
| Aluminum starch octenylsuccinate (Dry-Flo ® PC starch, a product of National Starch and Chemical Company) | 10.00 |
| Phase D | |
| Diazolidinyl urea | 0.20 |
| | 100.00 |

The ingredients in Phase B were combined and heated to 80° C. All of the ingredients of Phase A except the acrylate/t-octylpropenamide copolymer were combined and heated to 80° C. and then the acrylate copolymer slowly added. Phase A was then added to Phase B at 80° C., mixed for 30 minutes and then cooled to 40° C. The aluminum starch octenylsuccinate of Phase C was added to the A/B mixture and mixed thoroughly. Diazolidinyl urea of Phase D was added and the mixture cooled to room temperature.

The use of the starch Uv screen in the above lotion formulation was evaluated using the procedures described in "Sunscreen Drug Products for Over-the-Counter Human Drugs" issued by F.D.A. on Aug. 25, 1978 (Federal Register). In this procedure the effectiveness of the Uv screen was determined on human subjects by testing a 1 centimeter square section treated with a predetermined amount of lotion, exposing the treated area to UV light (150 watt Xenon Arc Solar Simulator, Solar Light Co.) for a set period of time and thereafter making a visual comparison with untreated and fully masked areas. The SPF (skin protection factor) is calculated by comparing the effects of radiation on protected skin with the unprotected skin.

The SPF of the sample lotion formulation prepared above was 5.82, as compared to the control which did not contain the starch sunscreen agent and had an SPF of 1.68 (see Example 2).

EXAMPLE 2

In order to compare the use of different starch materials as sunscreen agents, several formulations the same as Example 1, but containing different starches, as identified below, were prepared and tested for SPF as described in Example 1. The results are given below.

| Starch Description | Amount | SPF |
|---|---|---|
| Control | — | 1.68 |
| Potato | 10% | 3.90 |
| Rice | 10% | 3.42 |
| Tapioca | 10% | 3.27 |
| Corn | 10% | 3.81 |
| Hylon VII (70% Amylose) | 10% | 3.57 |
| Aluminum starch octenylsuccinate (Example 1) | 10% | 5.82 |
| Aluminum starch octenylsuccinate | 5% | 4.32 |
| Aluminum starch octenylsuccinate (+ 1% titanium dioxide) | 5% | 8.05 |

These results indicate the use of all the above noted various starch materials gave significant skin protection over the control formulation which contained no sunscreen agent. Further improvement was noted when combining titanium dioxide with the hydrophobic starch (aluminum starch octenylsuccinate).

EXAMPLE 3

Another sunscreen composition was formulated as a protection cream in the following manner:

|  | Parts by Weight |
|---|---|
| Phase A | |
| Octyl methoxycinnamate | 7.5 |
| PEG 40 stearate | 1.0 |
| Glyceryl stearate SE | 2.0 |
| Stearic acid T.P. | 3.0 |
| Cetyl alcohol | 1.0 |
| Tinoveil FIN - titanium dioxide/$C_{12-15}$ alcohols benzoate | 1.7 |
| Finsolv TN - $C_{12-15}$ alcohols benzoate | 5.0 |
| Cyclomethicone | 3.0 |
| Phenyl Trimethicone | 1.0 |
| Dimethicone copolyol | 1.0 |
| Phase B | |
| Deionized water | 32.8 |
| Triethanolamine (99%) | 4.0 |
| Acrylates/t-octylpropenamide copolymer | |
| 2-phenylbenzimidazole-5-sulfonic acid | 4.0 |
| Carbomer 940 (2% aqueous solution) | 25.0 |
| Phase C | |
| Propylene glycol | 3.0 |
| Aluminum starch octenylsuccinate | 3.0 |
| Phase D | |
| Propylene glycol, diazolidinyl urea, methyl paraben, propylparben | 1.0 |
| | 100.00 |

Triethanolamine and deionized water of Phase B were combined and heated to 60° C. and the acrylate/t-octylpropenamide copolymers slowly sifted in and the mixture heated to 80° C. When complete, the 2-phenylbenzimedazole-5-sulfonic acid and Carbomer 940 were sifted in and mixed.

Phase A was combined and heated to 80° C., added to Phase B at 80° C. and mixed for 15 to 30 minutes. The mixture was cooled to 40° C.

The aluminum starch octenylsuccinate of Phase C was slurried in propylene glycol, added to the A/B mixture and mixed thoroughly. Phase D was then added and the mixture cooled to room temperature.

What is claimed is:

1. A sunscreen composition comprising a pharmaceutically acceptable aqueous starch sunscreen carrier containing at least about 20% by weight of water, based on the weight of the composition and from about 0.5 to 30% by weight, based on the weight of the composition, of uncooked, granular starch as the sunscreen agent.

2. The composition of claim 1 wherein the sunscreen agent is a hydrophobically modified starch.

3. The composition of claim 3, wherein the starch sunscreen agent is an alkenyl succinate starch where the alkenyl group contains 5 to 22 carbon atoms.

4. The composition of claim 3 wherein the sunscreen agent is aluminum starch octenylsuccinate.

5. The composition of claim 1 wherein the carrier is an aqueous emulsion.

6. The composition of claim 5 wherein from about 2 to 15% by weight of the starch sunscreen agent is present.

7. The composition of claim 1 wherein the pharmaceutically acceptable aqueous based starch sunscreen carrier comprises from about 70 to 99.5% by weight, based on the weight of the composition.

8. The composition of claim 7 wherein the sunscreen agent is a hydrophobically modified starch.

9. The composition of claim 8 wherein the carrier is an aqueous emulsion.

10. The composition of claim 9 wherein from about 2 to 15% by weight of the starch sunscreen agent is present.

11. The composition of claim 8 wherein the starch sunscreen agent is alkenyl succinate starch where the alkenyl group contains 5 to 22 carbon atoms.

12. The composition of claim 11 wherein the sunscreen agent is aluminum starch octenylsuccinate.

13. The composition of claim 12 wherein the carrier is an aqueous emulsion.

14. The composition of claim 13 is wherein from about 2 to 15% by weight of the starch sunscreen agent is present.

15. The method of protecting the skin of a human from excessive exposure to ultraviolet radiation comprising topically applying an effective amount of the composition of claim 1 to the skin.

16. The method of claim 15 wherein the sunscreen agent is a hydrophobically modified starch.

17. The method of claim 16 wherein the starch sunscreen agent is an alkenyl succinate starch wherein the alkenyl group contains 5 to 22 carbon atoms.

18. The method of claim 17 wherein the sunscreen agent is aluminum starch octenyl succinate and is used in an amount of from about 2 to 15% by weight.

* * * * *